(12) United States Patent
Osterberg

(10) Patent No.: US 8,025,062 B2
(45) Date of Patent: Sep. 27, 2011

(54) CONDOM

(76) Inventor: Brian Osterberg, Petoskey, MI (US)

( * ) Notice: Subject to any disclaimer, the term of this patent is extended or adjusted under 35 U.S.C. 154(b) by 409 days.

(21) Appl. No.: 12/279,813

(22) PCT Filed: Feb. 19, 2007

(86) PCT No.: PCT/US2007/062383
§ 371 (c)(1),
(2), (4) Date: Aug. 18, 2008

(87) PCT Pub. No.: WO2007/098428
PCT Pub. Date: Aug. 30, 2007

(65) Prior Publication Data
US 2010/0218771 A1  Sep. 2, 2010

Related U.S. Application Data

(60) Provisional application No. 60/774,573, filed on Feb. 17, 2006.

(51) Int. Cl.
*A61F 6/04* (2006.01)
*A61F 6/02* (2006.01)
*A61F 5/44* (2006.01)

(52) U.S. Cl. .................. 128/844; 128/842; 604/349

(58) Field of Classification Search .................. 128/844, 128/918, 917, 842; D24/105; 604/349; 600/38, 600/39, 41
See application file for complete search history.

(56) References Cited

U.S. PATENT DOCUMENTS

| | | | |
|---|---|---|---|
| 6,223,747 B1 | 5/2001 | Rudge et al. | |
| 2004/0099274 A1* | 5/2004 | Osterberg | 128/844 |

\* cited by examiner

*Primary Examiner* — Patricia Bianco
*Assistant Examiner* — Victoria J Hicks
(74) *Attorney, Agent, or Firm* — Gifford, Krass, Sprinkle, Anderson & Citkowski, P.C.

(57) ABSTRACT

A condom is disclosed herein that may include a body having an open end, a closed end and at least a first region and a second region. The first region may have a first diameter and the second region may have a second diameter that is larger than the first diameter. Accordingly, during use, the second region may operate to repeatably slip or telescope over the first region.

13 Claims, 2 Drawing Sheets

CONDOM

CROSS-REFERENCE TO RELATED APPLICATIONS

This application claims priority to U.S. Provisional Patent Application Ser. No. 60/774,573 filed on Feb. 17, 2006, the content of which is incorporated herein by reference.

FIELD OF THE INVENTION

Disclosed herein is a male or female condom having a body with regions of different diameter. In use, the reciprocating movement of the body and/or changing length of an erect penis may result in a region having a larger diameter being at least partially folded or telescoped over (or onto) an adjacent region having a smaller diameter.

BACKGROUND OF THE INVENTION

It is generally desirable to maintain the open end of a condom as close as possible to the base of the penis on which the condom is positioned. Unfortunately, the natural shape of a male member (which is generally thicker at the base with an upward taper) and friction against the rolled condom outer ring (the normal outer ring of male condoms) caused by thrusting and pull-out may cause a condom to want to roll-up during use.

Prior art condoms may also permit uncontrolled bunching of material along random portions of the condom body. This indiscriminate bunching may occasionally form large masses of material in a single area. This unpredictable and unwanted large circumference of bunched material can create significant frictional adhesion between the penis and vaginal wall such that the entire condom is pulled up or tugged forward along the shaft of the penis to uncover or expose more of the base of the penis shaft. Another description would be to say that prior art condoms "ride up" along the shaft of the penis towards the tip of the penis. This "riding up" is a component in the condom the slipping off the penis during use (i.e., condom failure).

SUMMARY OF THE INVENTION

Disclosed herein is condom having a body that includes regions of different diameter. These regions of different diameter may function such that during use in intercourse the reciprocating movement of the condom body and/or a changing length of an erect penis may result in a region of a larger diameter being at least partially folded or telescoped over or onto an adjacent region having a smaller diameter.

These regions of varying size may be positioned along the length of the condom body, with the smallest diameter regions, or tightest-fitting regions typically (but not exclusively) being at specific points along the shaft including: 1) proximate the open end of the pouch; 2) at mid-point of the pouch; and/or 3) at a position on the pouch that, during use of the condom, would be located behind the glans penis.

Two components of the disclosed condom may also work together to hold the condom in place. First, tighter-fitting regions may keep the condom in place during use: 1) with an erection of varying length due to changing erectile state, particularly when comparing the full length of the actual condom pouch to the length of the erection, which can be the lesser of the two; 2) during a lessening of the erectile state of a male member; or 3) if one used a condom longer than need, which may cause excess condom material to bunch up.

Second, the larger diameter regions may help take up slack condom material in an overlapping manner (as opposed to random bunching at a single point). This may be similar to the effect of foreskin covering the glans penis while in a non-erect state. By way of example, the foreskin may slide forward and backward in an overlapping effect since the amount of loose skin is more than required to cover the length of the penis.

The condom may also be placed on a partially to semi-erect penis and held in place at the open end through a tight-fitting outer ring at the open end. Such an arrangement may allow the length of the condom pouch material to overlap along the length of the erection as needed. Further, any excess condom material may be operable to retract or extend itself in predetermined segments due to the differing circumference sizes along the length of the shaft.

Accordingly, the condom disclosed herein may rearrange its pouch material in a way to nullify excessive and uncontrolled bunching through the use of tight-fitting regions (e.g., less than or equal to the open end diameter of the condom) and regions of controlled overlapping of material. Both of these regions may reduce condom "pull-up or riding up" and thereby aid in keeping the penis covered as completely as possible to reduce instances of skin-on-skin contact between sexual partners. There may be less of an opportunity for a condom slip off and for condom failure. Furthermore, asymmetrical shaped or non-conventional non-straight-walled condoms (e.g., pouched or spiral designs) have increased the tendency of condoms to bunch up on the erect penis because of increased frictional adhesion along the shaft or condom tip. In fact, increased frictional adhesion is the intended purpose of these non-straight-walled, or special-shaped condoms. The condom disclosed here helps to alleviate this uncontrolled bunching, while maintaining or creating frictional adhesion by way of the condom's own folding action created by the various segments or regions. The disclosed condom may thus be used in conjunction with these non-conventional designs, as well as conventional regular straight-walled condoms. Finally, since male condom sizes in particular are often limited by standards of minimum and maximum lengths and widths, the condom disclose herein may assist in making these regulated condoms more adaptable to all wider variety of users of all sizes and varying degrees of erection.

As mentioned above, this disclosure is a Non-Provisional application of Provisional application 60/774,573, the disclosure of which is incorporated by reference herein in its entirety.

BRIEF DESCRIPTION OF THE DRAWINGS

Reference will now be had to the attached drawings wherein like reference numerals refer to like parts throughout and wherein.

DETAILED DESCRIPTION OF THE PREFERRED EMBODIMENTS

Figure 1:
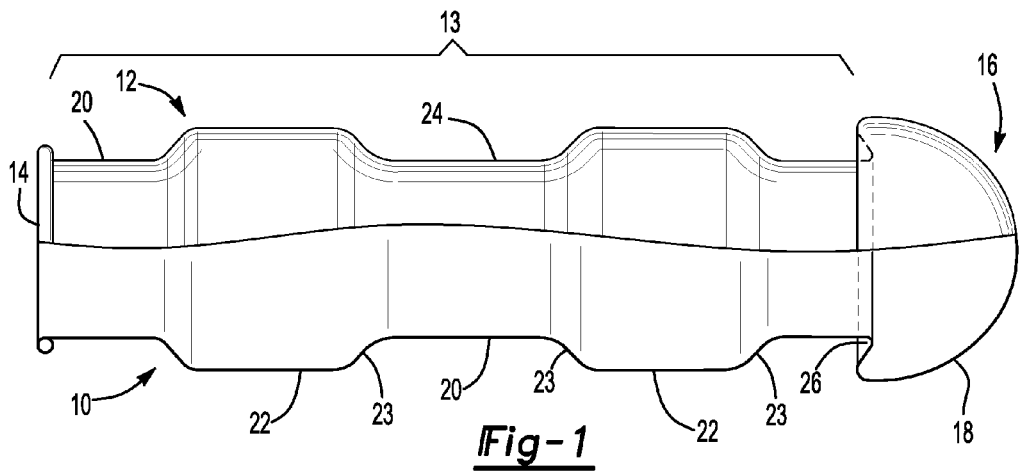
FIG. 1 is a side partial cutaway view of an embodiment of a condom.
Figure 2:
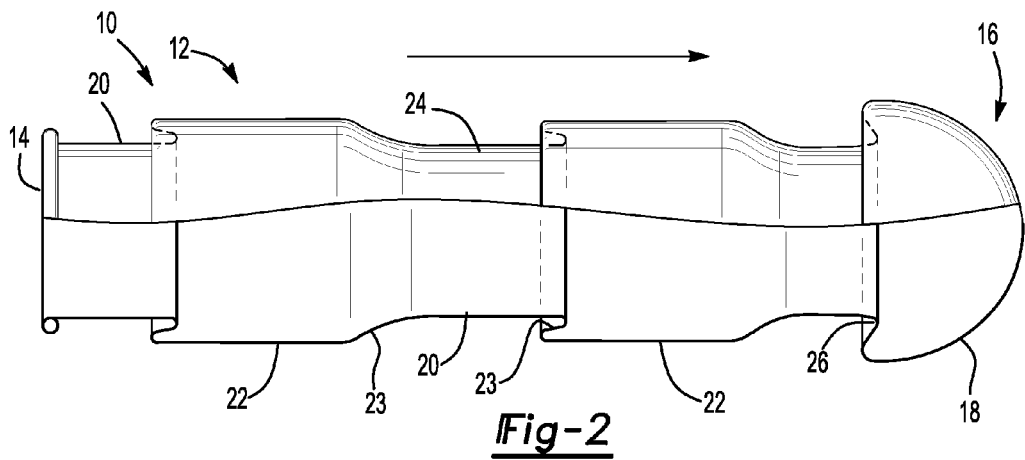
FIG. 2 is a side partial cutaway view of the embodiment of FIG. 1 as it may function during use.
Figure 6:
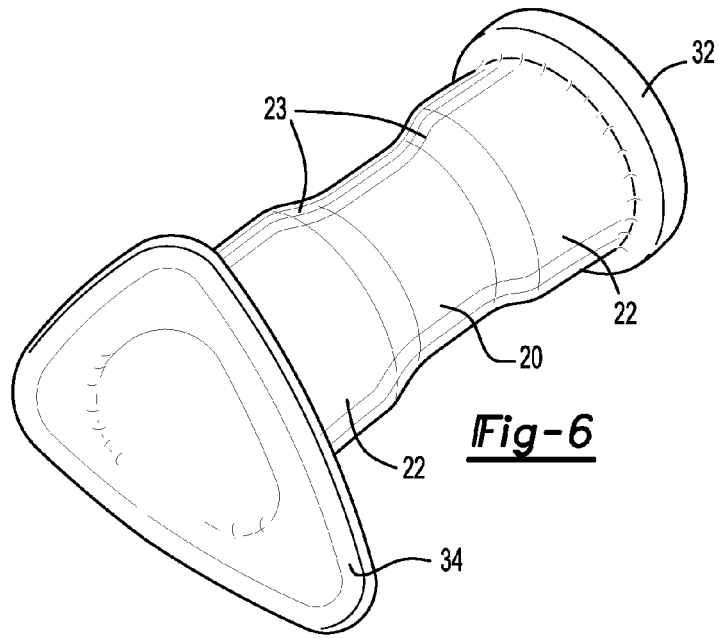
FIG. 6 is a perspective view of another embodiment of a condom.

Referring now to FIGS. 1 and 2, a condom 10 may include an elongated body 12 that may be positioned on the shaft of a male member (not shown) or vaginally inserted (see FIG. 6). The body 12 of the condom 10 may include an open end 14 and a closed end 16. A head portion 18 operable to contain the glans (not shown) of a male member may also be positioned at the closed end 16. The body 10 may have a first region(s) 20 having a first diameter and a second region(s) 22. The second region(s) 22 may have a second diameter that may be larger than the first diameter. The second regions 22 may also be positioned adjacent to or a predetermined distance away from a first region 20. Transition areas 23 of predetermined dimensions may also be provided to bridge regions of different diameter. By way nonrestrictive example, the regions 20, 22 may be bridged by a transition area 23 of the body 12 that may have a slope or angle of between about 20 to 70 degrees. Accordingly, during use of the condom 10 the reciprocal movement of the body 12 (or other actions such as a change in size of a male member) may cause the second region(s) 22 of the body 12 to briefly fold onto or over, in a telescoping fashion, the first region(s) 20.

Still referring to FIGS. 1 and 2, a wall 24 of the body 12 of the condom 10 may be constructed of latex. However, any other material known to be used in the manufacture of condoms may also be used in the construction of the condom 10. For example, the condom 10 may be constructed of commercially available polymers that are used in the production of adult sex toys.

Still referring to FIGS. 1 and 2, the body 12 of the condom 10 may include one or more first regions 20. The diameter of the first region(s) 20 should be sufficient to permit the body 12 to be retained in position on the male member during use. Further, to assist in the retention of the body 12 on a male member the first region(s) 20 may be positioned on the body 12 near the ends 14, 16 (i.e., proximate the open end 14 and the head portion 18 of the body 12.) However, as shown, the first region(s) 20 may also be positioned at any intermediate point along the body 12 between the open 14 and closed 16 ends of the condom 10. Additionally, it will be appreciated that during use the smallest or smaller diameter regions of body 12 of a male version of the condom 10 may also serve to snuggly engage a male member and thereby prevent or inhibit the migration of lubricant or other fluids toward the open end 14 of the condom 10. For example, a lubricant that may be initially located in the head 18 of a condom 10 may be prevented or inhibited from migrating toward or out of the open end 14 of the condom 10 by the use of a region having a diameter that may be designed to snuggly engage a male members and thereby dam up the lubricant in the head 18 of the condom 10. Likewise, in a female version of the condom 10 a smaller diameter region of the body 12 positioned proximate the closed end 16 may also have the effect of preventing and/or inhibiting the migration of a lubricant toward the open end 14.

Still referring to FIGS. 1 and 2, the body 12 of the condom 10 may also include one or more second regions 22 that may be positioned adjacent a first region(s) 20 or (as will be discussed below) another region of different diameter. As mentioned above, the second region(s) 22 may have a diameter that may be larger than the diameter of the first region(s) 20. As a result, the body 12 may not be retained on or otherwise tightly contact the male member in the area of the second region(s) 22. However, as best shown in FIG. 2, during use the larger diameter of the second region(s) 22 relative to an adjacent first region(s) 20 may result in the second region(s) 22 slipping or overlapping the first region(s) 20. Further, this slipping or overlapping of the first and second regions 20, 22 of the body 12 of the condom 10 may create a unique frictional sensation that may be transmitted to the user of the condom and his or her partner that may result in increased pleasure for both individuals.

Referring now to FIGS. 1 through 5, as mentioned above, the head portion 18 of the body 12 may have a diameter sufficient to permit containment of the glans of the male member. The head portion 18 may also include a base 26 or wall that, during use, may engage the sulcus (not shown) of the male member. To further assist in the retention of the condom 10 on the male member, the base 26 may also be angled toward (FIGS. 1, 2, 4 and 5) or away (FIG. 3) from the open end 14 of the body 12 (i.e., more or less than 90 degrees relative to the intersection of the base 26 and the shaft 13 of the body 12).

Figure 3:
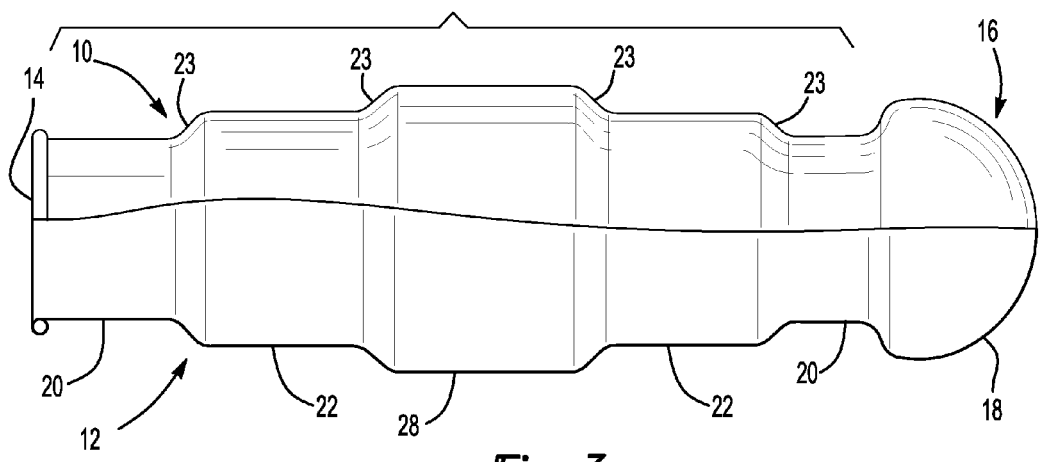
FIG. 3 is a side cutaway view of another embodiment of a condom.
Figure 4:
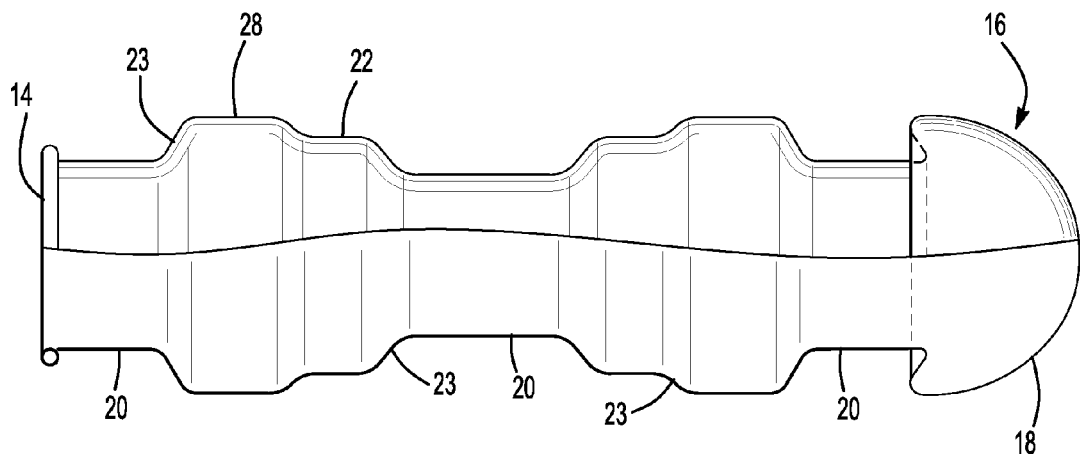
FIG. 4 is a side partial cutaway view of another embodiment of a condom.

Referring now to FIGS. 3 and 4, there is shown two further embodiments of the condom 10 that may have an open end 14 and a closed end 16 and a head portion 18. The body 10 may also include one or more first region(s) 20 having a first diameter, one or more second region(s) 22 adjacent the first region 20 that have a second diameter larger than the first diameter, and one or more third region(s) 28 adjacent the second region 22 that have a third diameter larger than the second diameter. However, as shown in FIG. 4, it will be appreciated that the condom 10 may be constructed such a third region may be adjacent a first region 20. Accordingly, as set forth above, during use the larger diameter of the third 28 region(s) may cause that region 28 to overlap an adjacent first 20 or second region 22. Likewise, the larger diameters of a second region(s) 22 may cause that region to overlap an adjacent first region(s) 20.

Figure 5:
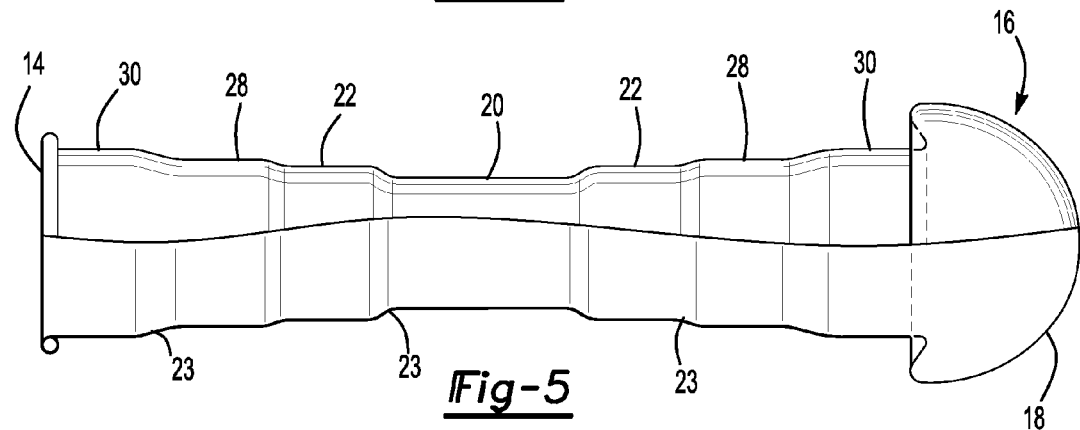
FIG. 5 is a side partial cutaway view of another embodiment of a condom.

Referring now to FIG. 5, there is shown a further embodiment of the condom 10 that may an open end 14 and a closed end 16 and a head portion 18. The body 10 may include one or more first region(s) 20 having a first diameter, one or more second region(s) 22 that have a second diameter larger than the first diameter, one or more third region(s) 28 that have a third diameter larger than the second diameter, and one or more fourth regions 30 that have a fourth diameter that may be larger than the third diameter. As such, it will be appreciated that the body 12 may include one or more regions along its length that have a diameter that may be smaller than the diameter of the ends 14, 16 of the condom. It will also be appreciated that the size of the fourth diameter in one embodiment of the invention may be the same as that of a first diameter in another embodiment. However, as mentioned above, in use the larger diameter regions may still function to slip and overlap the regions of smaller diameter.

Referring now to FIG. 6, there is shown a further embodiment of the condom 10, specifically a female version of the condom 10, which may have an open end 14 and a closed end 16. The closed end 16 may include a retaining device 32 for use in securing the condom 10 in position in a vagina (not shown). The open end 14 may also include a frame 34 that extends around the parameter of the open end 14. Further, as mentioned above, the body 12 of the condom 10 may include one or more first region(s) 20 having a first diameter and one or more second region(s) 22 adjacent the first region 20 that have a second diameter smaller than the first diameter. In use, the reciprocal movement of a male member (not shown) inside the body 12 of the condom 10 may cause the first region 20 to slip under the second region 22. This slipping action may, in turn, generate additional frictional adhesion and create a pleasurable sensation for the condom 10 user and his or her partner.

Finally, referring now to FIGS. 1 through 6, and by way of nonrestrictive example only, the diameter of the first, second, etc. regions disclosed herein for a typical male condom may be in the range of between 39 mm to 84 mm with the diameter of the regions for a typical female condom being in the range of between 20 mm and 110 mm. Further, the increase in diameter between adjacent regions may be in a range between about 1 mm to 30 mm with an increase of about 5 mm being a more typical example Likewise, the length of a particular region on the body 12 of the condom 10 may be in a range of between 1 mm to 60 mm, with a length of about 20 mm to 30 mm being a more typical example.

Having thus described my invention, various other embodiments will become known to those having skill in the art that do not depart from the spirit of the present invention.

The invention claimed is:

1. A condom comprising:
a male condom including an elongated body having an open end, a closed end, a first region, and a second region adjacent the first region with a transition area extending between the first region and the second region, the first region and having a first diameter and the second region and having a second diameter, the second diameter being larger than the first diameter, and the body being configured so that during use of the condom the second region of the body folds about the transition area so that the second region telescopes over the first region, whereby the condom acts against uncontrolled bunching of the body through the overlapping of the first region by the second region to thereby shorten the length of the condom.

2. The condom of claim 1, wherein the body further comprises a third region adjacent the second region and having a third diameter, the third diameter being larger than the second diameter, and the third region of the body being configured so that during use of the condom the third region telescopes over the second region.

3. The condom of claim 2, further comprising pair of first regions and a pair of third regions and wherein the pair of third regions are positioned along the body of the condom between the pair of first regions.

4. The condom of claim 3, wherein a first region is positioned along the body of the condom adjacent a third region.

5. The condom of claim 2, wherein the body further comprises a fourth region adjacent the third second region and having a fourth diameter, the fourth diameter being larger than the third diameter, and the fourth region of the body being configured so that during use of the condom the fourth region telescopes over the third region.

6. The condom of claim 2, further comprising a pair of second regions and wherein the third region is positioned between the pair of second regions.

7. The condom of claim 1, wherein the body further comprises a head portion.

8. The condom of claim 7, wherein the head portion further comprises a base operable to engage the sulcus of a male member.

9. The condom of claim 8, wherein the base of the head portion is angled toward the open end of the body.

10. The condom of claim 8, wherein the base of the head portion is angled away from the open end of the body.

11. The condom of claim 7, further comprising a fluid located within the head portion and wherein the first region is positioned along the body proximate the head portion.

12. The condom of claim 1, further comprising a pair of second regions and wherein the first region is positioned between the pair of second regions.

13. The condom of claim 1, further comprising a pair of first regions and a pair of second regions and wherein the pair of second regions are positioned between the pair of first regions.

* * * * *

UNITED STATES PATENT AND TRADEMARK OFFICE
CERTIFICATE OF CORRECTION

PATENT NO. : 8,025,062 B2
APPLICATION NO. : 12/279813
DATED : September 27, 2011
INVENTOR(S) : Brian Osterberg Page 1 of 1

It is certified that error appears in the above-identified patent and that said Letters Patent is hereby corrected as shown below:

Column 5, claim number 1, line number 20, after "region" delete "and".

Column 5, claim number 1, line number 21, before "having" delete "and".

Signed and Sealed this
Seventeenth Day of April, 2012

David J. Kappos
*Director of the United States Patent and Trademark Office*